United States Patent
Viebach et al.

(10) Patent No.: US 10,076,233 B2
(45) Date of Patent: Sep. 18, 2018

(54) DEVICE FOR TRANSMITTING A DEFLECTION MOVEMENT, ENDOSCOPE BENDING CONTROL UNIT, AND ENDOSCOPE

(71) Applicant: Digital Endoscopy GmbH, Friedberg (DE)

(72) Inventors: Thomas Viebach, Waidhofen (DE); Freidrich Pauker, Diedorf (DE)

(73) Assignee: Digital Endoscopy GmbH, Friedberg (DE)

( * ) Notice: Subject to any disclaimer, the term of this patent is extended or adjusted under 35 U.S.C. 154(b) by 165 days.

(21) Appl. No.: 15/033,064

(22) PCT Filed: Oct. 28, 2014

(86) PCT No.: PCT/EP2014/073066
§ 371 (c)(1),
(2) Date: Apr. 28, 2016

(87) PCT Pub. No.: WO2015/063053
PCT Pub. Date: May 7, 2015

(65) Prior Publication Data
US 2016/0249791 A1    Sep. 1, 2016

(30) Foreign Application Priority Data

Oct. 30, 2013  (DE) ........................ 10 2013 222 042

(51) Int. Cl.
*A61B 1/012*  (2006.01)
*A61B 1/00*  (2006.01)
*A61B 1/005*  (2006.01)

(52) U.S. Cl.
CPC ........ *A61B 1/00154* (2013.01); *A61B 1/0052* (2013.01); *A61B 1/0057* (2013.01);
(Continued)

(58) Field of Classification Search
CPC . A61B 1/00154; A61B 1/0052; A61B 1/0057; A61B 1/00128; A61B 1/0125;
(Continued)

(56) References Cited

U.S. PATENT DOCUMENTS 3,549,806 A    12/1970  Wood
3,605,725 A *  9/1971  Bentov ................ A61B 1/0052
                                                    600/434

(Continued)

FOREIGN PATENT DOCUMENTS

CN    1286664 A    3/2001
CN    2762381 Y    3/2006
(Continued)

OTHER PUBLICATIONS

Mar. 2, 2015 Int'l Search Report from related PCT App. No. PCT/EP2014/077938 (3 pgs).
(Continued)

*Primary Examiner* — Timothy J Neal
(74) *Attorney, Agent, or Firm* — Knobbe, Martens, Olson & Bear LLP (57) ABSTRACT

The invention refers to a deflection movement transmission device comprising
a control element (1) arranged at a proximal end of the deflection movement transmission device for effecting a deflection movement,
an elongate transmission guiding body (5), and
a bendable body (6) to be deflected that is arranged at a distal end of the deflection movement transmission device,
wherein the control element (1) comprises an inner channel (16) through which the bendable body (6) to be deflected is guidable.

10 Claims, 10 Drawing Sheets

(52) U.S. Cl.
CPC ...... *A61B 1/00128* (2013.01); *A61B 1/00133* (2013.01); *A61B 1/0125* (2013.01)

(58) Field of Classification Search
CPC ............ A61B 1/00133; A61B 1/00066; A61B 1/00039; A61B 1/0055
See application file for complete search history.

(56) References Cited

U.S. PATENT DOCUMENTS

| | | |
|---|---|---|
| 4,241,729 A | 12/1980 | Aoshiro |
| 4,404,963 A | 9/1983 | Kohri |
| 4,415,767 A | 11/1983 | Gill et al. |
| 4,670,009 A | 6/1987 | Bullock |
| 5,245,133 A | 9/1993 | DeCarlo et al. |
| 5,569,157 A | 10/1996 | Nakazawa et al. |
| 5,588,950 A | 12/1996 | Sano |
| 5,630,419 A | 5/1997 | Ranalletta |
| 6,383,132 B1 | 5/2002 | Wimmer |
| 6,547,722 B1 | 4/2003 | Higuma et al. |
| 6,582,361 B2 | 6/2003 | Hirano |
| 6,716,160 B2 | 4/2004 | Mitsumori |
| 7,179,223 B2 | 2/2007 | Motoki et al. |
| 7,198,599 B2 | 4/2007 | Goto et al. |
| 7,841,880 B2 | 11/2010 | Ikeda |
| 2001/0025135 A1 | 9/2001 | Naito et al. |
| 2002/0040180 A1 | 4/2002 | Hirano |
| 2002/0115907 A1 | 8/2002 | Mitsumori |
| 2003/0092965 A1* | 5/2003 | Konomura ......... A61B 1/00039 600/146 |
| 2004/0015050 A1 | 1/2004 | Goto et al. |
| 2005/0004434 A1 | 1/2005 | Bob et al. |
| 2006/0116550 A1 | 6/2006 | Noguchi |
| 2006/0135851 A1 | 6/2006 | Yamazaki |
| 2006/0199999 A1 | 9/2006 | Ikeda |
| 2006/0252993 A1* | 11/2006 | Freed ................... A61B 1/0052 600/146 |
| 2007/0156018 A1 | 7/2007 | Krauter et al. |
| 2007/0221701 A1* | 9/2007 | Ortiz ................... A61B 17/068 227/175.1 |
| 2007/0282371 A1* | 12/2007 | Lee ..................... A61B 17/062 606/205 |
| 2009/0209820 A1* | 8/2009 | Tanaka ................ A61B 1/0052 600/149 |
| 2009/0286412 A1 | 11/2009 | Ikeda |
| 2010/0168560 A1 | 7/2010 | Hauck et al. |
| 2011/0288372 A1 | 11/2011 | Petersen |
| 2011/0313252 A1 | 12/2011 | Lin |
| 2012/0170767 A1 | 7/2012 | Astrom et al. |
| 2012/0209068 A1 | 8/2012 | Hosaka |
| 2014/0148646 A1* | 5/2014 | Inada ..................... G05G 9/047 600/149 |
| 2015/0057537 A1 | 2/2015 | Dillon et al. |
| 2015/0173711 A1 | 6/2015 | Hiraoka |

FOREIGN PATENT DOCUMENTS

| | | |
|---|---|---|
| CN | 102307510 A | 1/2012 |
| CN | 102401995 A | 4/2012 |
| CN | 102697445 A | 10/2012 |
| CN | 202748535 U | 2/2013 |
| CN | 103153152 A | 6/2013 |
| CN | 103211566 A | 6/2013 |
| DE | 69 05 185 U | 4/1972 |
| DE | 34 46 698 A1 | 7/1985 |
| DE | 196 27 016 C1 | 2/1998 |
| DE | 697 25 670 T2 | 7/2004 |
| DE | 101 48 099 B4 | 6/2006 |
| DE | 10 2009 060 500 | 7/2011 |
| DE | 102010034623 | 2/2012 |
| DE | 10 2012 009332 | 11/2013 |
| EP | 0 028 396 B1 | 4/1981 |
| EP | 0055394 | 7/1982 |
| EP | 1475031 | 11/2004 |
| EP | 1 759 626 A2 | 3/2007 |
| ES | 2 356 497 | 4/2011 |
| JP | S 48 27116 | 8/1973 |
| JP | S 61 118713 | 6/1986 |
| JP | S 62 227312 | 10/1987 |
| JP | H 06254049 | 9/1994 |
| JP | 10-255439 | 8/1998 |
| JP | H11 244225 | 9/1999 |
| JP | A-2001-061772 | 3/2001 |
| JP | 2001510696 | 8/2001 |
| JP | 2002-160691 | 6/2002 |
| JP | 2002 291699 | 10/2002 |
| JP | 2003 190085 A | 7/2003 |
| JP | 2005 304 586 A | 11/2005 |
| JP | 2007 111541 A | 5/2007 |
| JP | 2007 252921 | 10/2007 |
| JP | 2007313047 | 12/2007 |
| JP | 2009 505688 A | 2/2009 |
| JP | 2009 101134 | 5/2009 |
| JP | 2009 530051 A | 8/2009 |
| JP | 2009 201762 | 9/2009 |
| JP | 2012 245058 A | 12/2012 |
| WO | WO 00/13569 A1 | 3/2000 |
| WO | WO 00/33727 | 6/2000 |
| WO | WO 2005/094665 A2 | 10/2005 |
| WO | WO2008056642 A1 | 5/2008 |
| WO | WO 2009/008596 | 1/2009 |
| WO | WO 2011/108157 A1 | 9/2011 |
| WO | WO 2011/114772 A1 | 9/2011 |
| WO | WO 2013/129204 | 9/2013 |

OTHER PUBLICATIONS

Mar. 24, 2015 Int'l Search Report from related PCT App. No. PCT/EP2015/051252 (4 pgs).
Apr. 30, 2015 Int'l Search Report from related PCT App. No. PCT/EP2015/051245 (6 pgs).
Anonymous: "Products I BMP-TAPPI", , Jun. 30, 2013 (Jun. 30, 2013), XP055394249, Gefunden im Internet: URL:https://web.archive.org/web/20130630082009/http :// www.bmp-tappi.com:80/products [gefunden am Jul. 27, 2017].
Anonymous: "10. Tappo per innesti rapidi femmina", , Jun. 22, 2013 (Jun. 22, 2013), XP055394266, Gefunden im Internet: U RL :https ://web.arch ive.o rglwebl 201 306221 61 7 34lhTtpl www. bmp-tappi. it:80/po rtfol io_item/tappo-per-i n. nesti- rapidifemmina [gefunden am Jul. 27, 2017].
Search Report for Application CN 2015800056419 in 2 pages (English translation).
Search Report for Application CN 2014800410593 in 2 pages (English translation).
Search Report for Application CN 201480076051 in 2 pages (English translation).
Office Action dated Sep. 4, 2017 in 7 pages for Chinese Application No. 201580005641.9 (English Translation).
International Search Report dated Oct. 8, 2014 for International Application No. PCT/EP2014/065587.
International Search Report dated Jan. 13, 2015 for International Application No. PCT/EP2014/073064.
International Search Report dated Jan. 13, 2015 for International Application No. PCT/EP2014/073066.
International Search Report dated Jan. 19, 2015 for International Application No. PCT/EP2014/073065.
International Search Report dated Mar. 24, 2015 for International Application No. PCT/EP2014/075902.

* cited by examiner

DEVICE FOR TRANSMITTING A DEFLECTION MOVEMENT, ENDOSCOPE BENDING CONTROL UNIT, AND ENDOSCOPE

CROSS REFERENCE TO RELATED APPLICATIONS

This application is a U.S. National Phase of PCT International Application No. PCT/EP2014/073066, filed Oct. 28, 2014 and which claims priority benefit of German Patent Application No. 102013222042.1 filed on Oct. 30, 2013. The entirety of each of the above-identified applications is hereby incorporated by reference.

BACKGROUND

Field of the Invention

The present invention relates to a deflection movement transmission device which transmits a deflecting movement effected by a control element to a reaction element. Moreover, the present invention relates to an endoscope bending controller and an endoscope.

Description of Related Art

Such deflection movement transmission devices may be used for a variety of purposes. One field of application of the deflection movement transmission device is an endoscope in which a bendable end of a catheter, i.e. a so-called deflecting portion (also designated as bending portion), is moved by pivoting a control element, with the movement of the deflecting portion precisely following the movement of the control element.

In medical examinations using an endoscope, the transmission of a pivoting movement of a control element to a bending movement of the deflecting portion should be as precise as possible. On the other hand, the transmission of a pivoting movement of a control element to a bending movement of the deflecting portion should be easily and straightforwardly executable for the operator.

SUMMARY

It is the object of the present invention to provide an improved deflection movement transmission device.

In particular, it is the object of the present invention to provide a deflection movement transmission device which is particularly favorable in functionality and easy to use. Moreover, an improved endoscope bending controller and an improved endoscope shall be provided.

According to the invention, this object is achieved by a deflection movement transmission device comprising the features of claim 1. Advantageous further developments are described in the dependent claims. An endoscope bending controller is shown in claim 10, and an endoscope is shown in claim 11.

Thus, the invention relates to a deflection movement transmission device comprising a control element arranged at a proximal end of the deflection movement transmission device for effecting a deflection movement, an elongate transmission guiding body, and a bendable body to be deflected that is arranged at a distal end of the deflection movement transmission device, the control element comprising an inner channel through which the bendable body to be deflected is guidable.

In this deflection movement transmission device, the bendable body to be deflected can be passed through the control element which controls the deflecting movement of the bendable body to be deflected. In this way, a deflection movement transmission device is provided which enables safe and straightforward handling of a bending movement of a deflecting portion (bending portion) within the narrowest of spaces.

The deflection movement transmission device can comprise a base body at which the control element for effecting a deflection movement is arranged such that a movement of the control element relative to the base body can be carried out, with the elongate transmission guiding body being arranged on one side of the base body, and the base body also comprising an inner channel through which the bendable body to be deflected is guidable. Thus, the bendable body to be deflected cannot only be passed through the control element but through the entire deflection movement transmission device.

In the deflection movement transmission device, the inner channel can be arranged concentrically in the control element, and/or the inner channel can be arranged concentrically in the base body. The stability of the entire device is not impaired by this. Moreover, the inner channel in the control element can comprise a funnel-shaped insertion opening as insertion aid. This allows safe guidance of the body passed therethrough.

In the deflection movement transmission device, at least a portion of the elongate transmission guiding body is guidable through the inner channel of the control element and/or the inner channel of the base body. Thus, not only a deflecting portion as a bendable body to be deflected, but also a transmission guiding body which transmits the bending movement to the deflecting portion can be passed through the deflection movement transmission device.

In the deflection movement transmission device, the control element can have a pivot portion that is supported on a head portion of the base body and is pivotable relative to the head portion of the base body for effecting a deflection movement, and at least one movement transmission wire body whose proximal end is articulated to the outer circumference of the pivot portion of the control element, wherein the movement transmission wire body is guided through the elongate transmission guiding body along the longitudinal direction thereof, the distal end of the movement transmission wire body is attached to the distal end of the bendable body to be deflected, and the pivot portion of the control element has an outlet opening of the inner channel of the control element, and the head portion of the base body has an inlet opening of the inner channel of the base body.

In the deflection movement transmission device, the control element can be configured as an actuating lever which, at the pivot portion, has a foot surface facing the base body, wherein the head portion of the base element has a front face facing the control element, wherein at least the foot surface of the pivot portion of the control element and/or the front face of the head portion of the base element is curved such that the foot surface can be rolled on the front face, wherein the pivot portion of the control element has the articulation point of the movement transmission wire body on its outer side, and, with its foot surface, is pivotably seated on the front face of the head portion of the base element, wherein the foot surface of the pivot portion comprises the outlet opening of the inner channel of the control element, and the front face of the head portion comprises the inlet opening of the inner channel of the base body.

In the deflection movement transmission device, the control element can be configured as an actuating lever which, at the pivot portion, turns into a hollow ball portion which is at least formed as a ball ring portion, wherein the head portion of the base element is formed spherically, wherein the hollow ball portion has the articulation point of the movement transmission wire body on its outer side and, on its inner ball surface, is slidably seated on the spherical head portion, wherein the hollow ball portion comprises the outlet opening of the inner channel of the control element and the spherical head portion comprises the inlet opening of the inner channel of the base body.

In the deflection movement transmission device, the control element can be lockable so as to lock a deflected position of the control element.

In the deflection movement transmission device, one, two, three, four or more movement transmission wire bodies can be provided, the first ends of which are equally spaced apart from each other and articulated to the control element, and the opposite second ends of which are fixed to the distal end portion of the body to be deflected in a corresponding manner equally spaced apart from each other.

The features of the invention can be combined in a suitable manner.

In the following, the invention will be explained in detail by means of examples.

DETAILED DESCRIPTION OF THE DRAWINGS

In the following, embodiments of the present invention will be described in detail by means of the drawings.

First Embodiment

First of all, a first embodiment of the present invention will be described in detail by means of FIGS. 1-7.

The first embodiment shows a deflection movement transmission device which is used in an endoscope for an endoscope bending control.

In the present embodiment, this deflection movement transmission device consists of a control element 1, plural wire bodies 2, a rod element 3 as base element, a rod element holder 4, a catheter tube 5 and a bendable body as deflecting portion (bending portion) 6.

The control element 1 consists of a hollow cylindrical element comprising a control head 12, on the bottom side of which a hollow shaft 13 is centrically arranged and turns into a hollow ball portion 11, on the outer surface of which the wire bodies 2 are anchored. On its side facing away from the head 12, the hollow ball portion 11 is open. In particular, the opening at the hollow ball portion 11 is such that the hollow ball portion 11 amounts to approximately 9/10 of a ball of which approximately 1/10 has been cut off.

Figure 1:
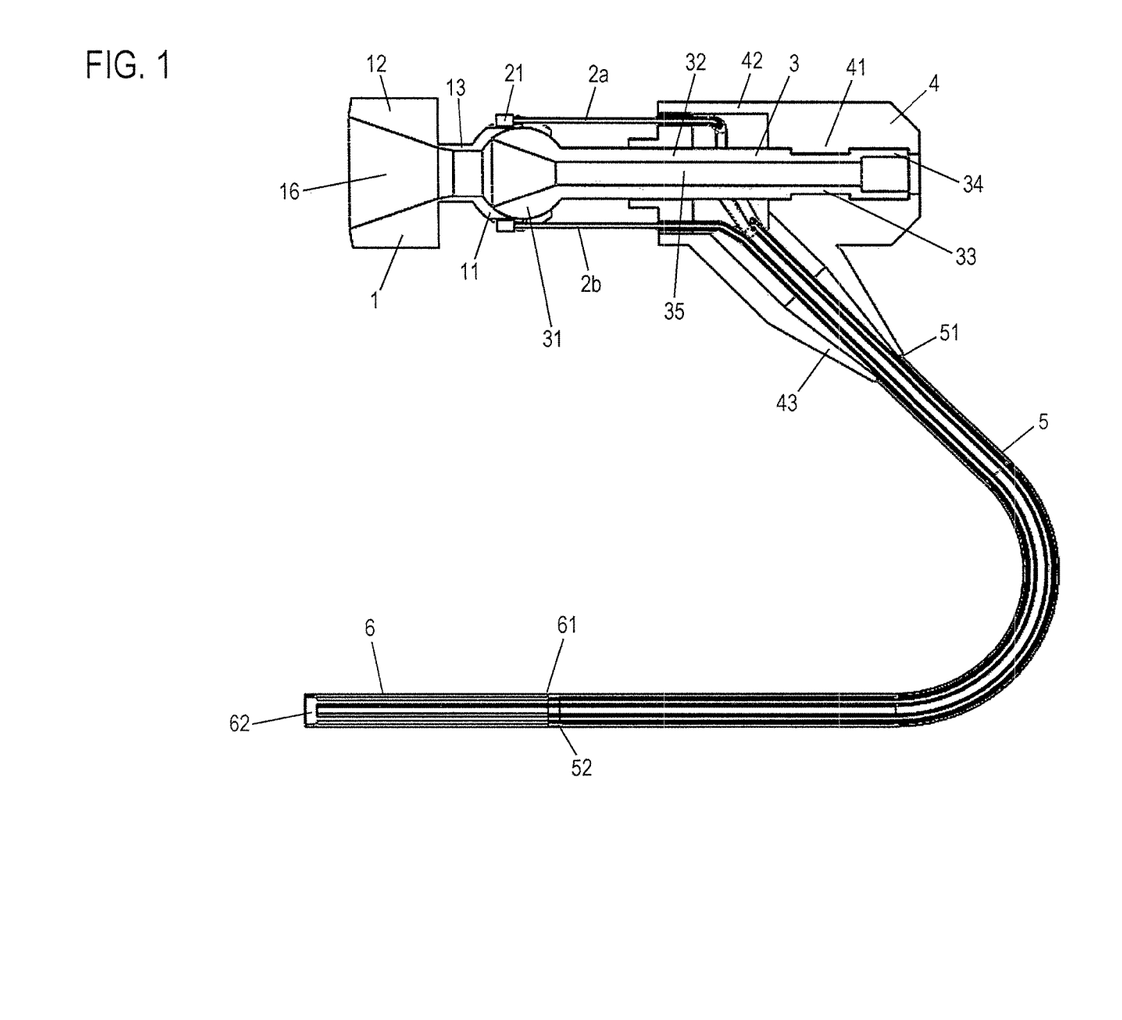
FIG. 1 shows a schematic sectional view of the deflection movement transmission device of a first embodiment in the non-deflected state.

The control element 1 is structured in a rotationally symmetrical configuration and comprises an inner channel 16 which concentrically extends through the head 12, the hollow shaft 13 and the hollow ball portion 11. The inner channel 16 is enlarged in the head 12 such that its inner diameter increases towards the side of the head 12 facing away from the hollow ball portion 11, as shown in FIG. 1. Thus, the inner channel 16 of the head 12 has a funnel-shaped inlet opening which is shown in FIG. 1 on the left side of the inner channel 16. The funnel-shaped inlet opening of the inner channel 16 facilitates the insertion of the deflecting portion 6 into the inner channel 16.

The control element 1 is made of a plastic material.

The control element 1 is seated as a joystick on a head 31 of the rod element 3. In particular, the hollow ball portion 11 of the control element 1 is seated on a counter-ball portion 31 which forms the head of the rod element 3. The counter-ball portion 31 is designed such that it has a ball shape of such a size that the hollow ball portion 11 seated thereon is smoothly movable. The dimensional relationship between the counter-ball portion 31 and the hollow ball portion 11 is such that a movement of the control element 1 relative to the rod element 3 is possible without any great effort on the part of the operator, although, on the other hand, the hollow ball portion 11 does not sit loosely on the counter-ball portion 31.

The rod element 3 has a longitudinal cylinder 32 which, on its distal side, turns into the counter-ball portion 31 and, at its distal end portion, comprises a screw end 34 which, in the present embodiment, is formed as an inner square. Proximally from the square end 34, the rod element 3 has an outer threaded portion 33 on its outer cylinder surface. The rod element 3 has a rotationally symmetrical configuration and, on the inside, it comprises an inner channel 35 which extends concentrically through the counter-ball portion 31, the longitudinal cylinder 32 and the square end 34. Incidentally, the counter-ball portion 31, the longitudinal cylinder 32 and the square end 34 are formed as an integral rod element. The longitudinal cylinder 32 of the rod element 3 is designed as a cylinder having a smooth outer surface, with the exception of the threaded portion 33 provided thereon.

At the counter-ball portion 31, the inner channel 35 has a funnel-shaped inlet opening which is represented on the left side of the inner channel 35 in FIG. 1. The funnel-shaped inlet opening of the inner channel 35 is opposite to the outlet opening of the inner channel 16 at the hollow ball portion 11 and facilitates the insertion of the deflecting portion 6 into the inner channel 35.

As is shown in the figures, the rod element 3 is seated in a rod element holder 4. The rod element holder 4 consists of a cylinder element 42 having a rotationally symmetrical configuration and a centric inner channel. The cylinder element 42 in particular comprises a hollow space facing the control element 1 and a bottom on the side of the rod element holder 4 facing away from the control element 1. More precisely, the bottom of the rod element holder 4 comprises the concentric inner channel. In the concentric inner channel, an internal thread 41 is formed. As is schematically indicated in the figures, the outer thread 33 of the rod element 3 is seated on the inner thread 41 of the rod element holder 4, wherein, by a screwing movement, the rod element 3 can be concentrically screwed in or out relative to the rod element holder 4. For the purpose of carrying out the screwing movement, an appropriate tool is inserted into the square end 34 of the rod element 3. Other relative movement techniques are possible, as is represented under "Alternatives" at the end of the description.

On its outer circumferential side, the cylinder element 42 of the rod element holder 4 has a catheter connecting element 43. In the present embodiment, the catheter connecting element 43 extends relative to the cylinder element 42 of the rod element 4 under an acute angle, as can be seen from the drawings.

In particular, the catheter connecting element 43 is formed as a round hollow profile which basically represents a channel branch from the distal hollow space of the cylinder element 42. The catheter connecting element 43 is formed cylindrically, tapering in the direction away from the cylinder element 42. On the inside, the catheter connecting element 43 comprises a concentric channel in which the wire bodies 2 are guided. At its distal end, the catheter connecting element 43 comprises a circular port.

The catheter tube 5 is fixed to the circular port of the catheter connecting element 43. In particular, the proximal end 51 of the catheter tube 5 is seated at the port of the catheter connecting element 43. At its distal end, the catheter tube comprises a ring 52 accommodated therein. The ring 52 forms the distal end of the catheter tube and the transition to the deflecting portion 6.

The deflecting portion 6 is a bendable body which is made of an elastic material in the known manner. At its proximal end, the deflecting portion comprises a deflecting connection 61 at which it is connected to the ring 52 of the catheter tube 5. At the distal end, the deflecting portion comprises a deflecting cap 62 at which a camera, a laser and/or a camera, etc. are arranged. Further functional units can be integrated at the deflecting cap 62.

Figure 4:
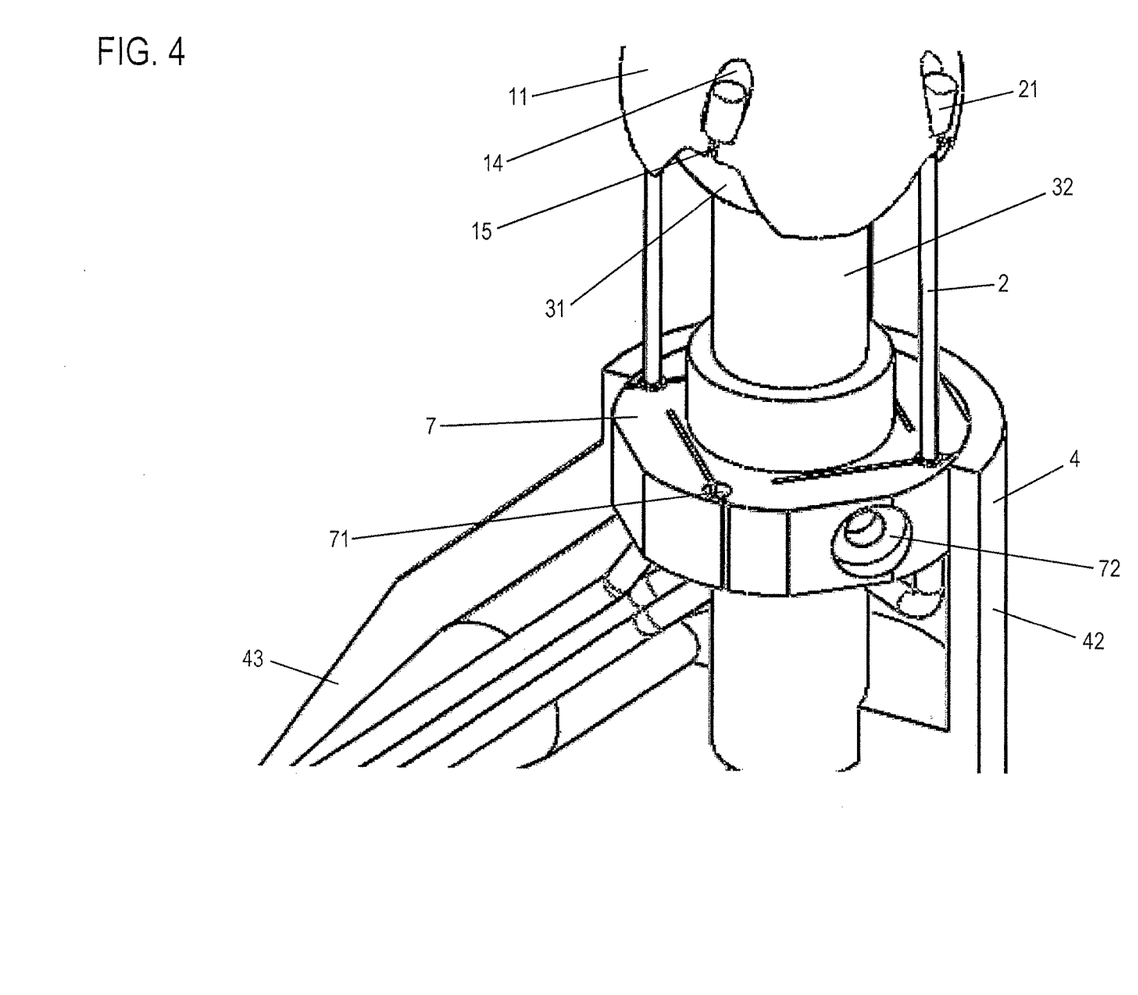
FIG. 4, in a schematic partial representation in perspective, shows details of the connection of the wire bodies to the control element and how the wire bodies are guided to the catheter tube.
Figure 5:
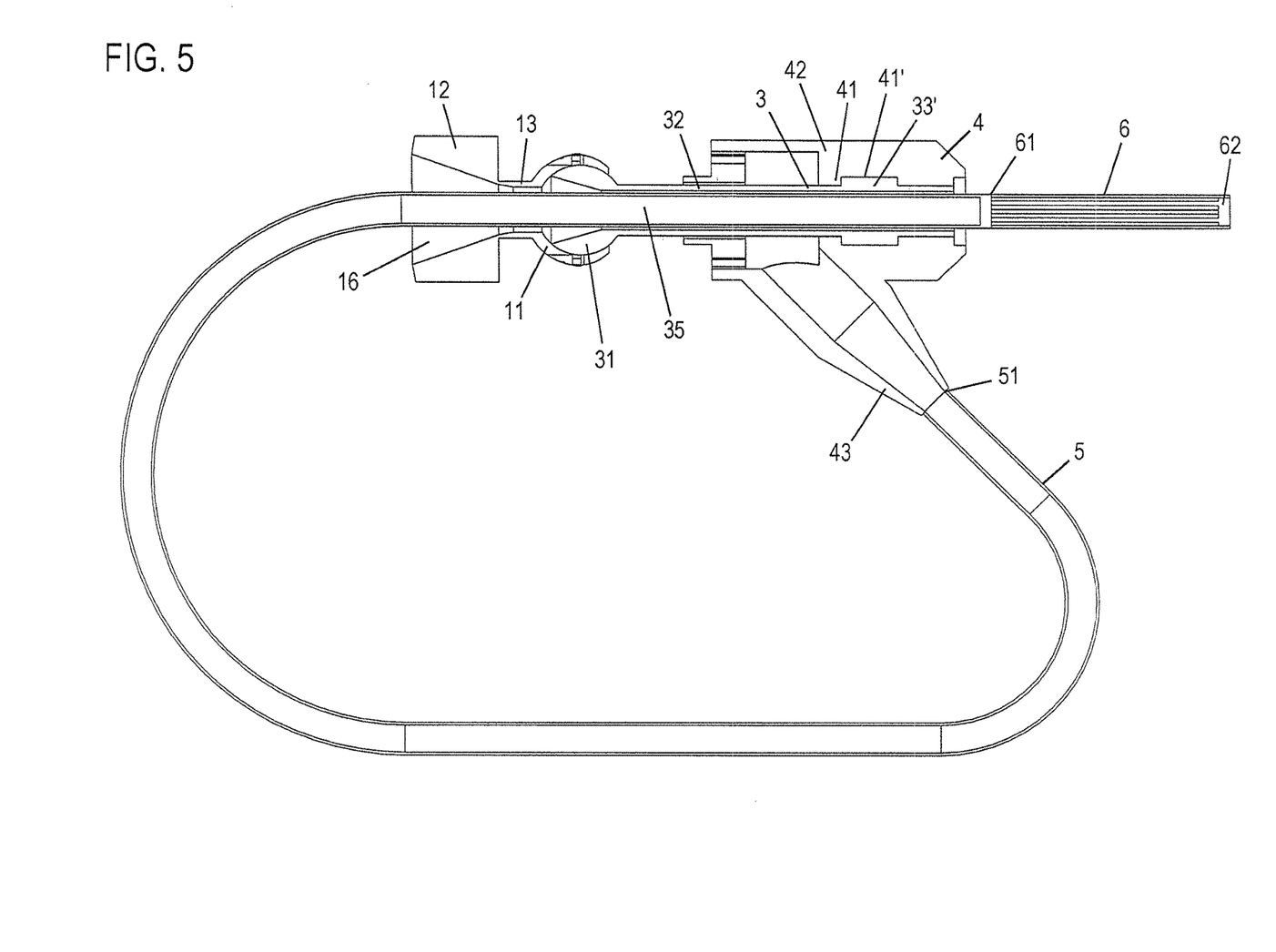
FIG. 5 shows a schematic sectional representation of the deflection movement transmission device of the first embodiment, with the catheter tube being guided through the deflection movement transmission device and not being deflected.
Figure 6:
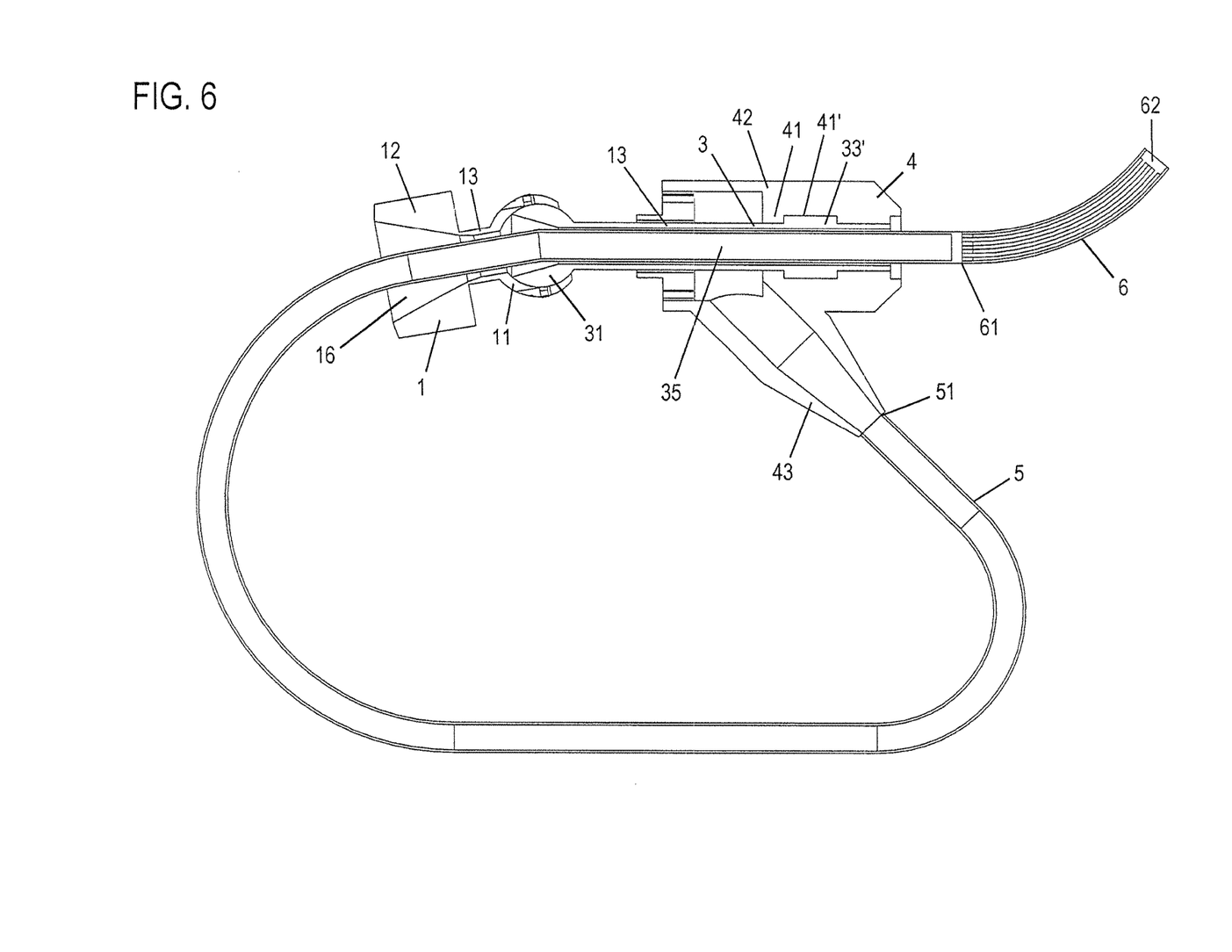
FIG. 6 shows a schematic sectional representation of the deflection movement transmission device, with the catheter tube being guided through the deflection movement transmission device and a deflection to the left taking place.
Figure 7:
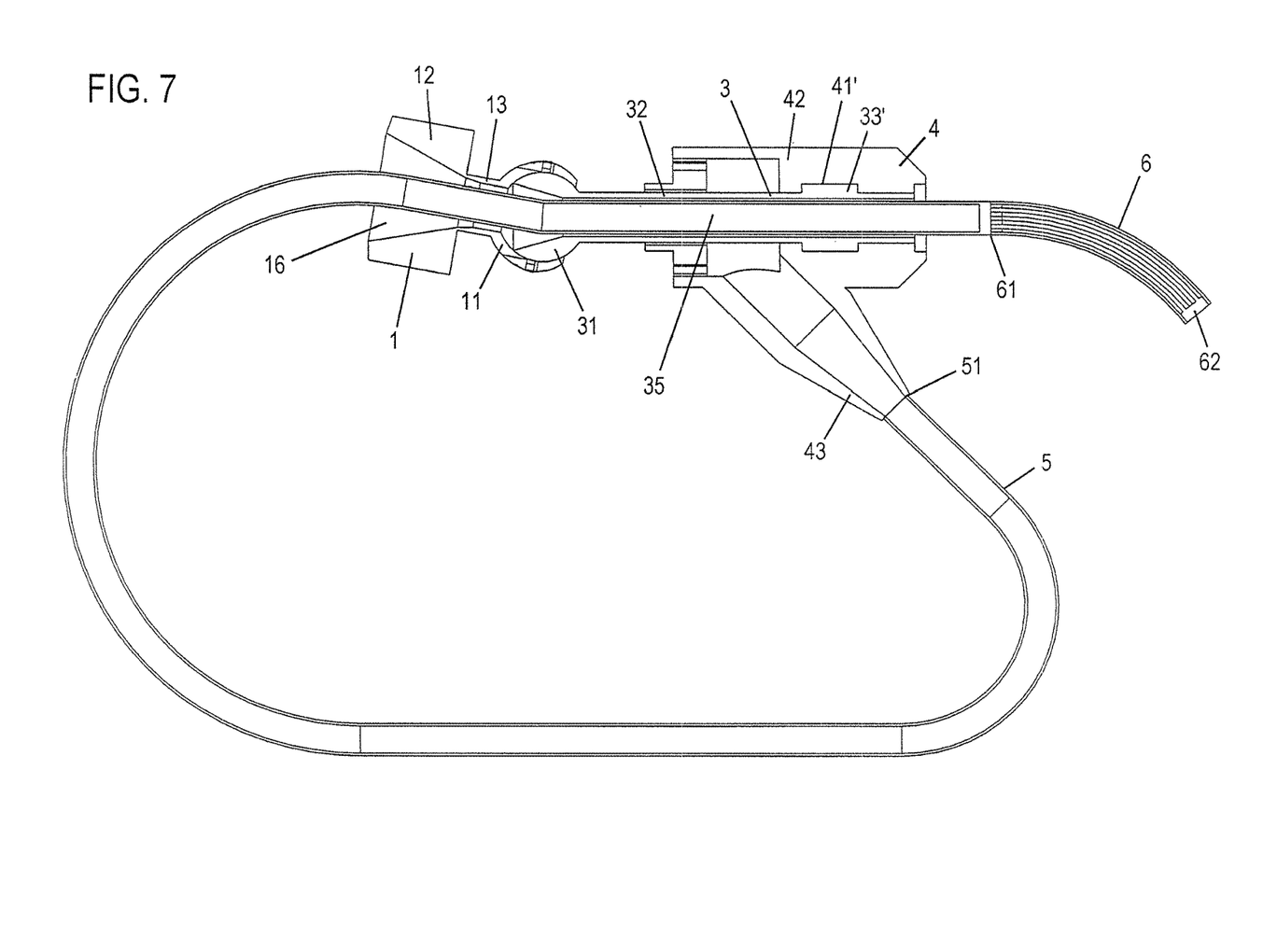
FIG. 7 shows a schematic sectional representation of the deflection movement transmission device, with the catheter tube being guided through the deflection movement transmission device and a deflection to the right taking place.

In a schematic partial representation in perspective, FIG. 4 shows details of the connection of the wire bodies to the control element and how the wire bodies are guided to the catheter tube. For the sake of clarity, the front left wire body 2 has been omitted in FIG. 4.

As shown in FIG. 4, several hang-in cavities 14 are provided on the outer circumferential surface of the hollow ball portion 11 on the equatorial line of the hollow ball portion 11. In the present embodiment, four hang-in cavities 14 are provided on the equator of the hollow ball portion 11. In particular, the hang-in cavities 14 are recesses formed in the hollow ball portion 11, the recesses being circular in cross section and having a bottom that extends approximately perpendicular to a bore hole direction of the hang-in cavity 14 and is positioned on the equatorial line, more specifically perpendicular to the equator of the hollow ball portion 11. When making the hang-in cavity 14, the hollow ball portion 11 can be drilled from the proximal side, so that the hang-in cavity is formed on the outer circumferential surface of the hollow ball portion 11 as a blind hole open at the side. Here, any other manufacturing processes are possible. The outer diameter of the hang-in cavity 14 is selected such that a barrel nipple 21 of the wire body 2 fits in the hang-in cavity 14. On the bottom of the hang-in cavity 14, i.e. at the distal end of the hang-in cavity 14, a channel 15 is formed as wire body hang-in, the channel extending coaxially to the longitudinal extension of the control element 1 and having a diameter larger than the outer diameter of the wire body 2, but smaller than the outer diameter of the barrel nipple 21 of the wire 2. In other words, similar to Bowden cable mountings on bicycles, the hang-in cavity 14 and the wire body hang-in 15 are provided such that a barrel nipple 21 of a wire body 2 can be hung thereinto. In a hung-in state of the wire body 2, the barrel nipple forms the proximal end of the wire body 2.

Figure 2:
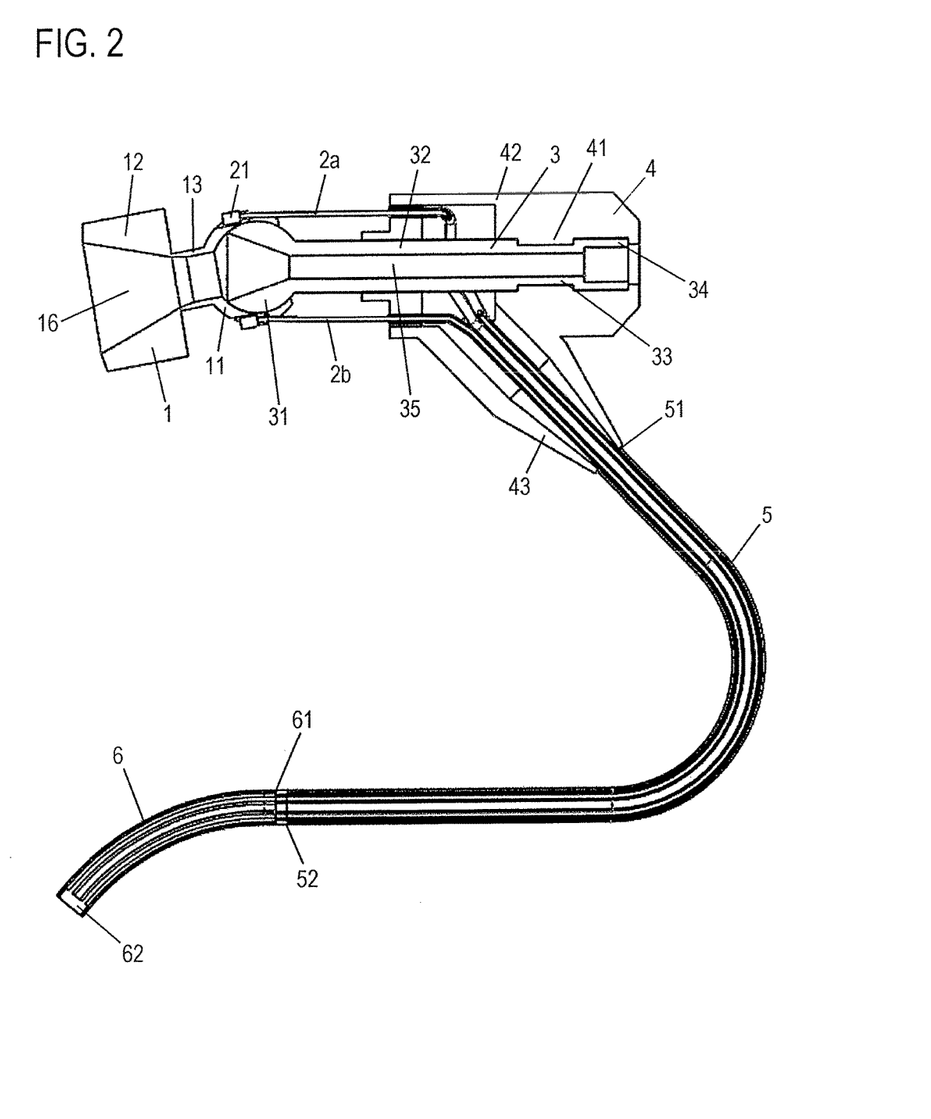
FIG. 2 shows a schematic sectional view of the deflection movement transmission device when deflected to the left.
Figure 3:
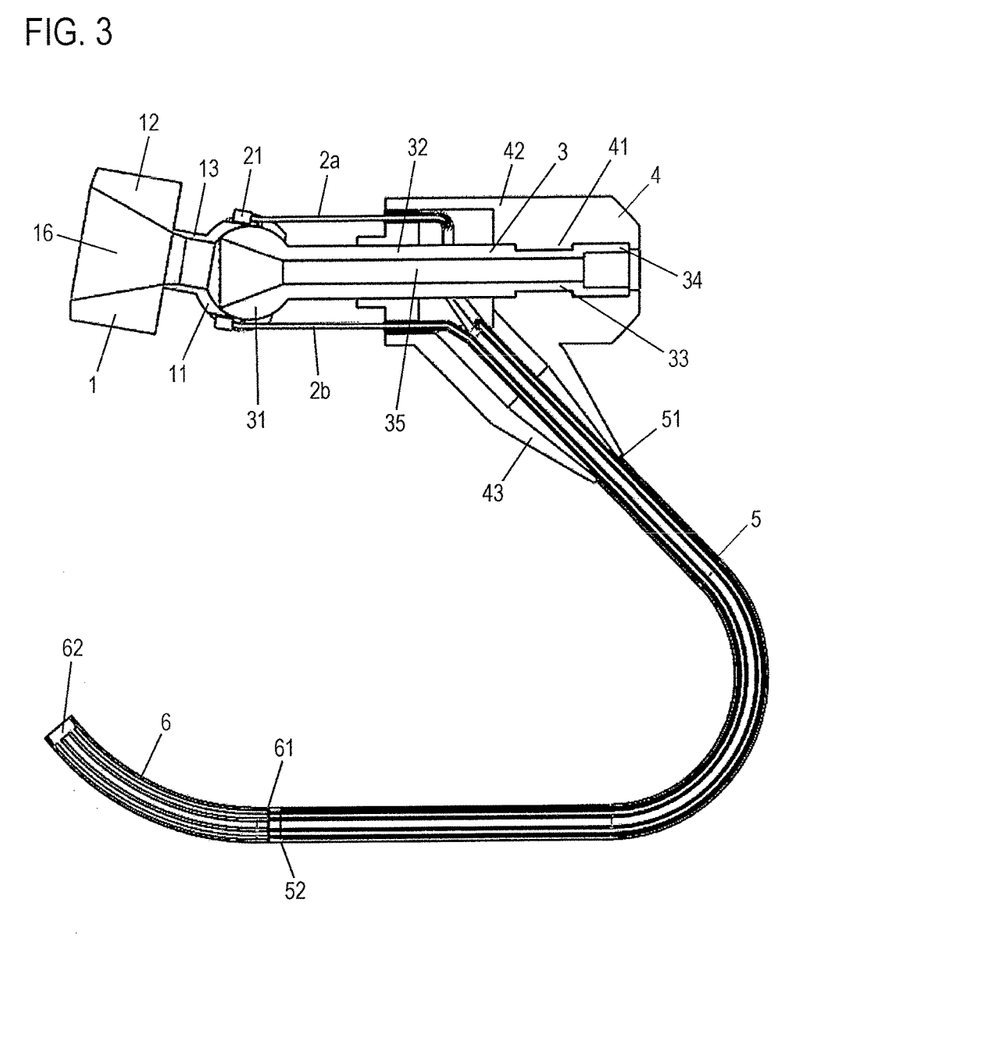
FIG. 3 shows a schematic sectional view of the deflection movement transmission device when deflected to the right.

In the present embodiment, four wire bodies 2 are provided, of which two wire bodies, i.e. the wire body 2a and the wire body 2b, are represented in each of FIGS. 1 to 3. The number of wire bodies 2 is not limited here. There may be provided one wire body 2, two, three, four or more wire bodies. If two or more wire bodies 2 are provided, the corresponding hang-in cavities 14 are arranged on the equator of the hollow ball portion 11 in a manner equally spaced apart from each other.

As is shown in FIG. 4, the cylinder element 42 comprises the opening to the hollow space of the cylinder element at its proximal end, i.e. at its end facing the control element 1. A wire body guiding ring 7 is inserted into this opening such that the proximal surface, i.e. the surface of the wire guiding ring 7 facing the control element 1, is aligned with the proximal front face of the cylinder element 42, which faces the control element 1. The wire guiding ring 7 is provided with tangential slits in the same number as there are wire bodies 2, as is shown in FIG. 4. Wire guiding bores 71 extending coaxially to the common axis of the control element 1, rod element 4 and cylinder element 42 of the rod element holder 4 are drilled into the slits. More specifically, the distance between each hang-in cavity 14 and the center axis of the control element 1 is exactly the same as the radial distance between the wire guiding bore 71 and the center axis of the wire guiding ring 7.

The wire bodies 2 are guided through the catheter tube 5 and through the ring 52 of the catheter tube and are anchored at the deflecting cap 62 of the deflecting portion 6. In particular, the wire bodies 2 are anchored at the deflecting cap 62 such that they are equally spaced apart from each other and are arranged, i.e. fixed, in the same order as on the hollow ball portion 11.

The ring 52 comprises openings for the wire bodies 2 in a corresponding manner as in the design of the wire guiding ring 7.

Mode of Operation

The control element 1 can be operated as a joystick, wherein its hollow ball portion 11 can be moved on the counter-ball portion 31 of the rod element 3. A pivoting operation of the joystick 1 relative to the rod element 3 in any direction whatsoever is possible in this way. By means of the wire bodies 2 arranged at the deflecting cap 62, the direction and the extent of the deflecting movement of the joystick 1 relative to the rod element 3 is then transmitted to the deflecting portion 6 formed as a bendable body. In other words, if the joystick 1 is moved to the left relative to the rod element 3, the deflecting portion performs a movement directed to the left, as is shown in FIG. 2. If the joystick 1 is moved to the right relative to the rod element 3, the deflecting portion performs a movement directed to the right, as is the case in FIG. 3.

Before the deflecting portion 6 is inserted, the control element 1 is put straight so that the deflecting portion 6 and the portion of the catheter tube 5 adjacent to the deflecting portion 6 are straightly aligned. The distal end (at the deflecting cap 62) of the deflecting portion 6 is inserted into the funnel-shaped inlet opening of the inner channel 16 in the control element 1, is slid through the inner channel 16, is inserted into the funnel-shaped inlet opening of the inner channel 35 in the rod element 3, and is slid through the inner channel 35 until the deflecting portion 6 emerges at the outlet opening of the inner channel 35 which is opposite to the funnel-shaped inlet opening of the inner channel 35.

When the deflecting portion 6 has reached its intended operating position, i.e. the position in which it has been slid through the deflection movement transmission device, the deflecting portion 6 can be brought into the desired position by pivoting the control element 1 in the desired direction and to the desired extent. The control element 1 as joystick may pivot in all directions and, consequently, the deflecting portion 6 cannot only pivot to the right and to the left, but in all directions.

Second Embodiment

In the following, a second embodiment of the present invention will be described in detail by means of FIGS. 8-10.

The second embodiment shows a deflection movement transmission device which is also used in an endoscope for an endoscope bending control.

Also in the present embodiment, this deflection movement transmission device consists of a control element 100, plural wire bodies (not shown in the drawings) in a similar manner as in the first embodiment, a rod element 300 as base element, a rod element holder 400, a catheter tube 500 and a bendable body as deflecting portion 600.

The control element 100 consists of a cylindrical element comprising a control head 120 on the bottom side of which a shaft portion 13 is centrically arranged. At the end opposite to the control head 120, the shaft portion 130 comprises a foot portion 110. The shaft portion 130 has an unchanging outer diameter. The foot portion 110 has an outer diameter which increases in the direction opposite to the control head 120.

The control element 100 has a rotationally symmetrical configuration and comprises an inner channel 160 which concentrically extends through the head 120, the shaft portion 130 and the foot portion 110. The inner channel 160 is enlarged in the head 120 such that its inner diameter increases towards the side facing away from the foot portion 110, as shown in FIG. 9. Thus, the inner channel 160 of the head 120 has a funnel-shaped inlet opening, which is shown in FIG. 9 on the left side of the inner channel 160. The funnel-shaped inlet opening of the inner channel 160 facilitates the insertion of the deflecting portion 600 into the inner channel 160. The funnel-shaped inlet opening of the inner channel 160 is rounded and consequently does not have any sharp edges.

At the foot portion 110, the control element 100 pivots relative to the rod element 300; therefore, the foot portion 110 of the control element 100 is referred to as pivot portion 110.

On the side opposite to the control head 120, the pivot portion 110 has an end surface formed as foot surface 110A. In the present embodiment, the foot surface 110A is curved outwardly, i.e. it is curved outwards opposite to the front face of the control head 120 which comprises the funnel-shaped inlet opening of the inner channel 160. In other words, the distance measured in the longitudinal direction of the cylindrical control element 100 between the foot surface 110A and the front face of the control head 120 opposite to the foot increases from the outer circumference towards the middle. Thus, the foot surface 110A forms a portion of a ball surface having a predetermined radius whose center lies on the imaginary extended axis of the control element 100.

The inner channel 160 has its outlet opening on the foot surface 110A. The inner channel 160 tapers in the area of the foot portion 110 and reaches its smallest inner diameter at the foot surface 110A. At the outlet opening, the inner channel 160 is rounded and consequently does not have any sharp edges.

At this narrowest position, the inner channel 160 has an inner diameter which, on the one hand, still allows a safe sliding-through of the deflecting portion 600 and the catheter tube 500 and, on the other hand, forms a guide for the deflecting portion 600 and the catheter tube 500 when these are passed through.

Figure 9:
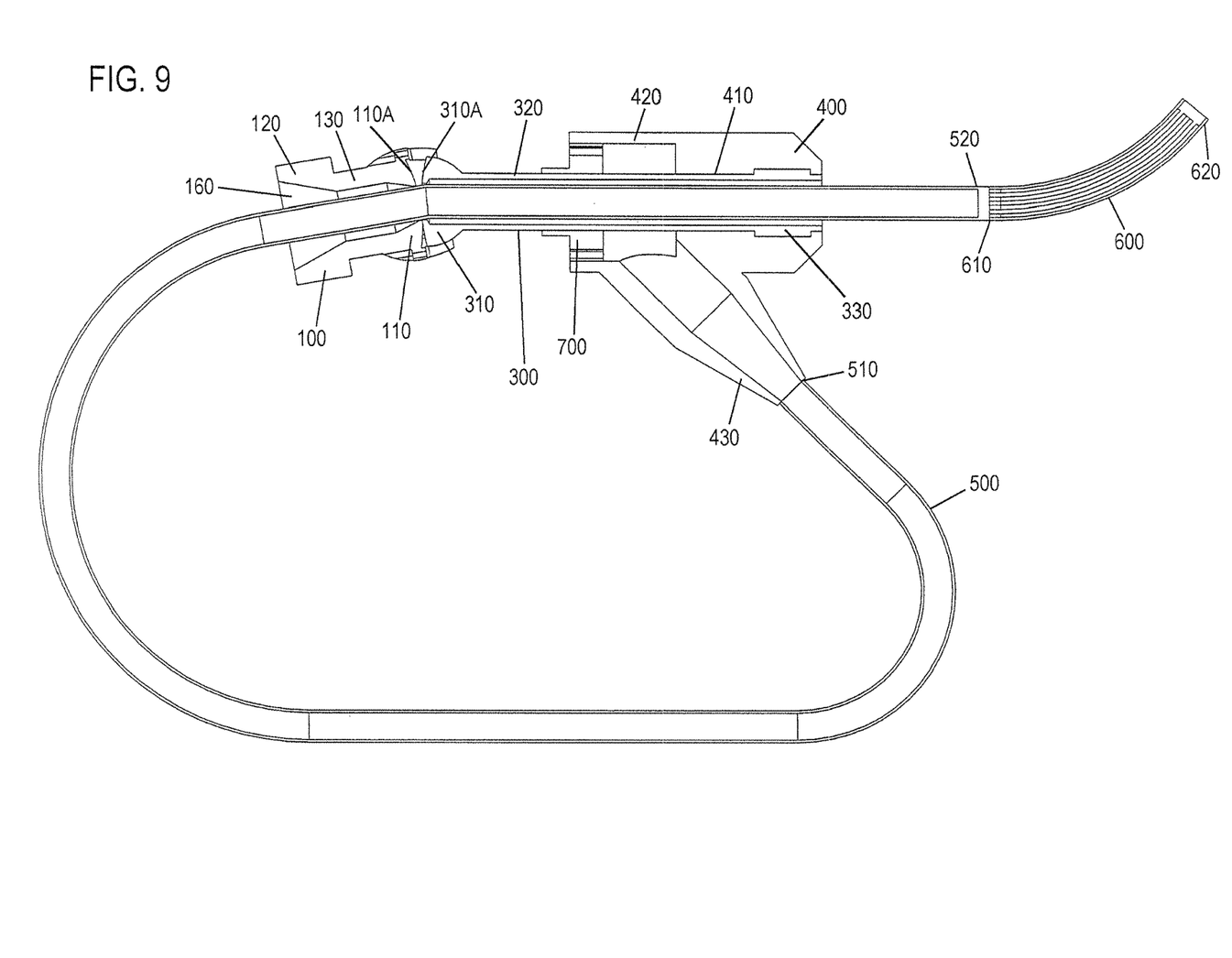
FIG. 9 shows a schematic sectional representation of the deflection movement transmission device of the second embodiment, with the catheter tube being guided through the deflection movement transmission device and a deflection to the left taking place.
Figure 10:
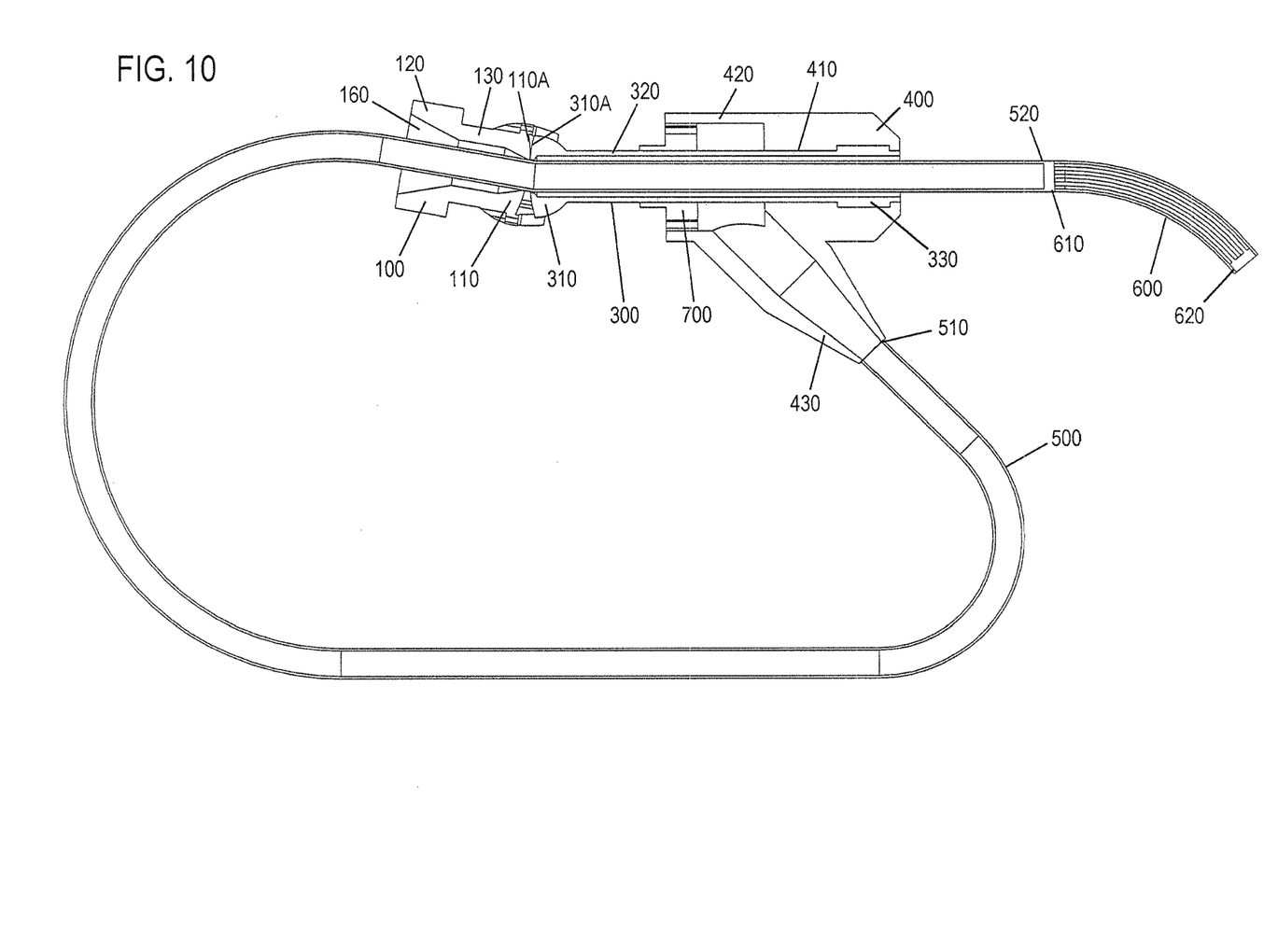
FIG. 10 shows a schematic sectional representation of the deflection movement transmission device of the second embodiment, with the catheter tube being guided through the deflection movement transmission device and a deflection to the right taking place.

The control element 100 has a rotationally symmetrical configuration, as is evident from FIGS. 9-11. The control element 100 is made of a plastic material but may also be made of metal.

Figure 8:
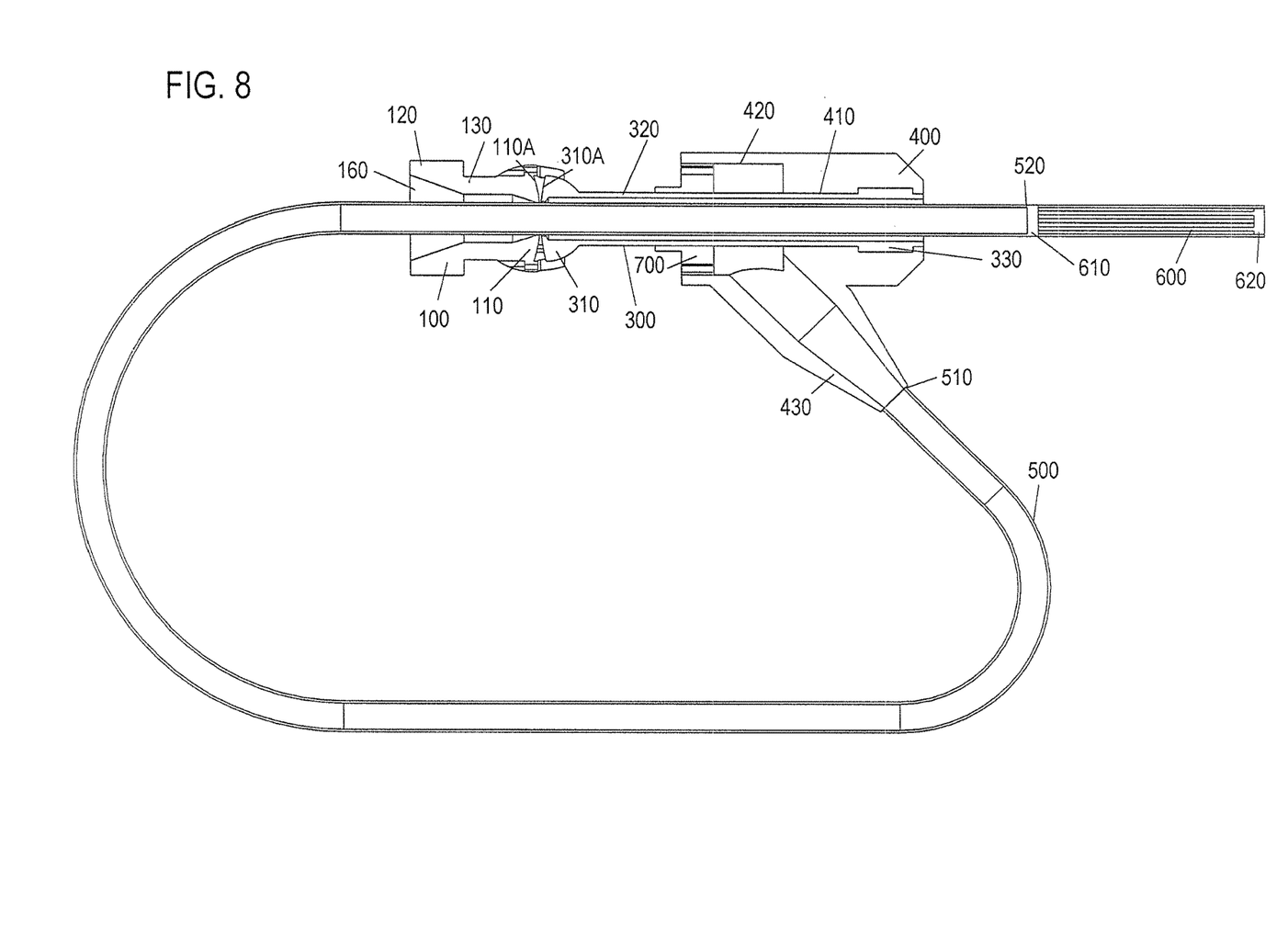
FIG. 8 shows a schematic sectional view of the deflection movement transmission device of a second embodiment, with the catheter tube being guided through the deflection movement transmission device and not being deflected.

The foot surface 110A of the pivot portion 110 faces a front face 310A of a head portion 310 of the rod element 300, as is shown in FIGS. 8-10.

The rod element 300 has a longitudinal cylinder 320 which, on its proximal side, turns into the head portion 310 and, in the vicinity of its distal end portion, has an increased diameter portion 330. The increased diameter portion 330 is provided as a cylinder portion which has a larger outer diameter than in the portion between the head portion 310 and the increased diameter portion 330. The rod element 300 has a rotationally symmetrical configuration.

Thus, the rod element 300 is an integral elongate element which comprises the head portion 310, the longitudinal cylinder 320 and the increased diameter portion 330. The longitudinal cylinder 320 of the rod element 300 is formed with a smooth outer surface.

The rod element 300 has a rotationally symmetrical configuration and comprises an inner channel 350 which concentrically extends through the head portion 310, the longitudinal cylinder 320 and the increased diameter portion 330. The inner channel 350 is narrowed at the head portion 310. At the front face 310A of the head portion 310, the inner channel 350 has its inlet opening where the inner channel 350 has its smallest inner diameter. At the inlet opening, the inner channel 350 is rounded and consequently does not have any sharp edges. Downstream of the inlet opening, the inner channel 350 has a uniform inner diameter which is larger than at the head portion 310. The inner channel 350 is also rounded at the outlet opening and does consequently not have any sharp edges. On the one hand, the narrowing of the inner diameter at the head portion 310 still allows a safe sliding-through of the deflecting portion 600 and the catheter tube 500 and, on the other hand, forms a guide for the deflecting portion 600 and the catheter tube 500 when these are passed through.

In the present embodiment, the front face 310A is also curved outwardly towards the control element 100. In other words, the front face 310A rises from the outer circumference towards the middle in the direction toward the control element 100. The front face 310A forms a portion of a ball surface having a predetermined radius whose center lies on the imaginary extended axis of the rod element 300.

The foot surface 110A and the front face 310A face each other and are in contact with each other. Hence, the pivot portion 110 of the control element 100 is, with its foot surface 110A, pivotably seated on the front face 310A of the head portion 310 of the rod element 300. In other words, the foot surface 110A can roll on the front face 310A.

In the non-pivoted state, the pivot portion 110 of the control element 100 and the head portion 310 of the rod element 300 lie on the same center axis since, in the non-pivoted state, the control element 100 and the rod element 300 are arranged coaxially to each other. Hence, in the non-pivoted state, the foot surface 110A and the front face 310A make contact with each other at a circular line, as is shown in FIG. 9. When the control element 100 is pivoted, as is shown in FIGS. 10 and 11, i.e. the pivot portion 110 is inclined relative to the head portion 310 of the rod element 300, the foot surface 110A rolls on the front face 310A. Here, it is noted that the representation in the drawings is merely schematic.

Thus, the control element 100 is seated as a joystick on the head portion 310 of the rod element 300.

The rod element 300 is arranged in the rod element holder 400. The rod element holder 400 is formed as a cylinder element 420 that has a rotationally symmetrical configuration. On the side facing the control element 100, the cylinder element 420 has a hollow space and on the side of the rod element holder 400 facing away from the control element 100, it has a bottom. The bottom of the rod element holder 400 has a concentric inner channel 410. At a portion of the concentric inner channel 410, a hollow space is formed in which the increased diameter portion 330 of the rod element 300 is seated. The axial end surfaces of the hollow space in the vicinity of the bottom of the rod element holder 400 form respective stoppers for the axial end surfaces of the increased diameter portion 330. Thus, in this embodiment, the rod element 300 cannot move axially, or it can only move with a small amount of play, relative to the rod element holder 400.

At a portion of its outer circumferential side, the cylinder element 420 of the rod element holder 400 has a catheter connecting element 430. In the present embodiment, the catheter connecting element 430 extends under an acute angle relative to the cylinder element 420 of the rod element 400, as becomes apparent from the drawings.

In particular, the catheter connecting element 430 is formed as a round hollow profile which basically represents a channel branch from the distal hollow space of the cylinder element 420. The catheter connecting element 430 is formed cylindrically, tapering in the direction away from the cylinder element 420. Inside, the catheter connecting element 430 has a concentric channel in which the wire bodies are guided. At its distal end, the catheter connecting element 430 has a circular port.

The catheter tube 500 is attached to the circular port of the catheter connecting element 430. In particular, the proximal end 510 of the catheter tube 500 is provided at the port of the catheter connecting element 430.

At its distal end, the catheter tube comprises a ring 520 accommodated therein. The ring 520 forms the distal end of the catheter tube and the transition to the deflecting portion 600.

The catheter tube 500 and the deflecting portion 600 are configured similar to the catheter tube 5 and the deflecting portion 6 of the first embodiment.

Similar to FIG. 4, also in the second embodiment, the wire elements are hung into in hang-in cavities of the control element. The description in connection with the wire elements of the first embodiment also applies to the second embodiment and will not be repeated here. The structure, the guidance and the mode of operation of the wire elements are the same.

In the second embodiment, merely the wire guiding ring 700 has a further function in addition to its structure described in the first embodiment. The wire guiding ring 700 as such is designed as in the first embodiment. The wire guiding ring 700 of the second embodiment is longitudinally movable with respect to the cylinder element 420 of the rod element holder 400. For this purpose, the cylinder element 420 of the rod element holder 400 comprises an axial longitudinal slit, not shown in the drawings, along which the fixing screw, which engages into the threaded hole 72 (FIG. 4) and which can fix the wire guiding ring 700 to the cylinder element 420 of the rod element holder 400, can be screwed tightly at different positions.

In this connection, the wires can be tensioned by the ring element 700 being shifted in an axial direction into the hollow space of the cylinder element 420 of the rod element holder 400 and then being locked by means of a locking element. In doing so, the angle of the deflection point of the wires changes at the outlet of the ring element 700; i.e. on the right side of the ring element 700 in FIG. 8. In other words, when the wires are tensioned, the obtuse angle of the deflection point of the wires at the downstream outlet of the ring element 700 is decreased between the extension of the wires from the hang-in point to the ring element 700 and the extension of the wires from the ring element 700 to the catheter tube 500. In this way, small tension lengths of the wires can be realized.

The wire bodies are guided through the catheter tube 500 and through the ring 520 of the catheter tube and are anchored at the deflecting cap 620 of the deflecting portion 600. In particular, the wire bodies are anchored at the deflecting cap 620 such that they are equally spaced apart from each other and are arranged in the same order as at the pivot portion 110.

The ring 520 comprises openings for the wire bodies in a corresponding manner as in the design of the wire guiding ring 700.

The length of each wire body from the fixing point at the deflecting cap 620 to the fixing point at the pivot portion 110 is always the same.

Mode of Operation

Similar as in the first embodiment, also the control element 100 of the second embodiment can be operated as a joystick, with the foot surface 110A of the hollow ball portion 110 rolling on the front face 310A of the head portion 310. A pivoting operation of the joystick 100 relative to the rod element 300 in any direction whatsoever is possible in this way. By means of the wire bodies arranged at the deflecting cap 620, the direction and the extent of the deflecting movement of the joystick 100 relative to the rod element 300 is then transmitted to the deflecting portion 600 formed as a bendable body.

If the joystick 100 is moved to the left relative to the rod element 300, the deflecting portion 600 performs a movement directed to the left, as is shown in FIG. 9. If the joystick 100 is moved to the right relative to the rod element 300, the deflecting portion 600 performs a movement directed to the right, as is shown in FIG. 10.

Before the deflecting portion 600 is inserted, the control element 100 is put straight so that the deflecting portion 600 and the portion of the catheter tube 500 adjacent to the deflecting portion 600 are straightly aligned. The distal end (at the deflecting cap 620) of the deflecting portion 600 is inserted into the funnel-shaped inlet opening of the inner channel 160 in the control element 100, is slid through the inner channel 160, is inserted into the inlet opening of the inner channel 350 in the rod element 300, which inlet opening is adjacent to the outlet opening of the inner channel 160, and is slid through the inner channel 350 until the deflecting portion 600 emerges at the outlet opening of the inner channel 350 opposite to the funnel-shaped inlet opening of the inner channel 350.

When the deflecting portion 600 has reached its intended operating position, i.e. the position in which it has been slid through the deflection movement transmission device, the deflecting portion 600 can be brought into the desired position by pivoting the control element 100 in the desired direction and to the desired extent.

Alternatives

The wire body 2 is hung into the hang-in cavity 14, which is shown in FIG. 4, in the form of a barrel nipple 21. The invention is not restricted to a barrel nipple and the nipple 21 can be designed as a known pear nipple; any similar nipples may be used. The shape of the hang-in cavity 14 can be adapted to the selected nipple shape.

In the first embodiment, the size of the hollow ball portion 11 has been selected such that it amounts to approximately 9/10 of a ball. The invention is not restricted to this. Any hollow ball shape size of the hollow ball portion 11 can be selected as long as the same can still perform the pivoting movement on the counter-ball portion 31. The hollow ball portion 11 may also have the shape of a hollow ball ring portion that extends by a predetermined minimum amount in parallel to the axial direction of the control element 1 on both sides of the equatorial line and basically forms an equatorial band.

In the second embodiment, the foot surface 110A is curved outwardly. Furthermore, the front face 310A of the head portion 310 is curved outwardly. The invention is not restricted to this. By using the principle of the invention, the deflection movement transmission device can also be constructed such that the foot surface 110A is designed to be plane and the front face 310A is curved outwardly. On the other hand, the deflection movement transmission device can also be constructed such that the foot surface 110A is curved outwardly and the front face 310A is designed to be plane. A construction in which the front face 310A is curved inwardly and the foot surface 110A is curved outwardly is also possible, as long as the radius of curvature of the front face 310A is larger than the radius of curvature of the foot surface 110A. In a similar manner, the front face 310A can be curved outwardly and the foot surface 110A can be curved inwardly, as long as the radius of curvature of the front face 310A is smaller than the radius of curvature of the foot surface 110A. It is merely sufficient that the foot surface 110A can roll on the front face 310A safely and in a controlled manner.

In the first embodiment, the square end 34 serves to enable a screwing movement for performing a movement of the rod element 3 relative to the rod element holder 4 at the threaded portions 33 and 41 in order to tension the wire bodies 2. The invention is not restricted to the square shape at the end 34 of the rod element 3. A triangular shape, an octagonal shape, or another polygonal shape can be selected. Basically any shape that enables the application of a torque generating the rotational movement of the rod element at the end 34 can be selected.

In the first embodiment, the movement of the rod element 3 relative to the rod element holder 4 is effected by the threaded portions 33 and 41. By means of the movement of the rod element 3 relative to the rod element holder 4, the wire bodies 2 are tensioned. Any other way of movement of the rod element 3 with respect to the rod element holder 4 may be selected for this purpose. For example, the rod element holder 4 may have a continuous inner cylinder hole and the rod element 3 may have a continuous cylindrical longitudinal cylinder 32, with a pulling device being attached to the end 34 of the rod element 3. A threaded hole may be provided in the rod element holder 4 perpendicular to the axis of the rod element holder, with a locking screw adapted to lock the longitudinal cylinder 32 in any position relative to the rod element holder 4 being seated in the threaded hole.

In the first embodiment, the rod element 3 can be concentrically screwed in or out relative to the rod element holder 4 by a screwing movement during which the inner thread 41 of the rod element holder 4 is in threaded engagement with the outer thread 33 of the rod element 3. In this design, the wires 2 can be tensioned by the rod element 3 being moved and locked relative to the rod element holder 4.

In the second embodiment, the rod element 300 is seated in the rod element holder 400 in which the increased diameter portion 330 is arranged in a hollow space of the rod element holder 400 provided for the same. Here, the distal and proximal end faces of the increased diameter portion 330 respectively form a stopper at the hollow space of the rod element holder 400. In this design, the wires can be tensioned by the ring element 700 being shifted in the axial direction into the hollow space of the cylinder element 420 of the rod element holder 400 and then being locked by means of a locking element.

The invention is not restricted to this. In the first embodiment, the wire tensioning possibility provided for the second embodiment may be applied; and in the second embodiment, the wire tensioning possibility provided for the first embodiment may be applied.

In the embodiments, the catheter connecting element 43; 430 extends under an acute angle, in consideration of the figures, to the rod element holder 4; 400. The invention is not restricted to this. Any extension angle of the catheter connecting element 43 with respect to the rod element holder can be selected.

In the embodiments, the catheter tube 5; 500 is a transmission guiding body having a hollow space in which the movement transmission wire body is guided. During a pivoting movement of the control element, the movement transmission wire bodies 2 are subjected to pulling forces and pushing forces. If these pulling forces and pushing forces are exerted on the same, the movement transmission wire bodies 2 must be adapted to slide on the transmission guiding body. Here, the transmission guiding body may have a closed cross section as is the case in a catheter tube 5; 500. The invention is not restricted to this. The transmission guiding body may be a rail element or a box element, on which the movement transmission wire body is guided. The cross section of the transmission guiding body may be open on the side on which the movement transmission wire bodies 2 do not slide.

The control element 1; 100 can be lockable in order to lock a deflected position of the control element 1; 100. In the first embodiment, the locking may take place by a locking screw which, for example, penetrates the hollow ball portion 11 and engages at the surface of the counter-ball portion 31, thereby acting as a friction brake in such a way that a particular deflected position of the control element 1, i.e. the control lever, is lockable by means of a friction brake. Moreover, locking can take place in all embodiments by clamping the movement transmission wire body/bodies 2 at the wire guiding ring 7; 700 or at the cylinder element 42; 420 of the rod element holder 4; 400, for example. If all wires 2 are locked, for example, by a locking clamp attached to the wire guiding ring 7; 700 or the cylinder element 42; 420, safe locking of a deflected position of the control element 1; 100 is achieved thereby. Other technical possibilities for blocking the wires 2 may be selected.

In the embodiments, the deflection movement transmission device is applied to an endoscope bending control in an endoscope. The deflection movement transmission device can also be applied in other technical fields. A use in water-conducting channels, mining tunnels, etc. is possible. The invention can be applied anywhere where pivoting movements are converted into deflecting movements of a deflection element.

LIST OF REFERENCE SIGNS

1 control element; joystick
2, 2a, 2b wire body
3 base element; rod element
4 rod element holder
5 catheter tube
6 bendable body, deflecting portion
7 wire guiding ring
11 hollow ball portion
11A foot surface of the hollow ball portion 11
12 head of the control element 1
13 shaft portion
14 hang-in cavity
15 wire body hang-in
16 inner channel in the control element
21 barrel nipple
31 head portion; counter-ball portion
31A front face of the head portion 31
32 longitudinal cylinder
33 threaded portion of the rod element 3
34 square end; distal end of the rod element 3
35 inner channel in the rod element
41 threaded portion of the rod element holder 4
42 cylinder element
43 catheter connecting element
51 catheter tube connection
52 ring
61 deflecting connection
62 deflecting cap
71 wire guiding bore
72 threaded hole for a fixing screw
100 control element; joystick
110 hollow ball portion
110A foot surface of hollow ball portion 110
120 head of the control element 100
130 shaft portion
160 inner channel in the control element
300 base element; rod element
310 head portion; counter-ball portion
310A front face of the head portion 31
320 longitudinal cylinder
330 increased diameter portion
350 inner channel in the rod element
400 rod element holder
410 inner channel in the rod element
420 cylinder element
430 catheter connecting element
500 catheter tube
510 catheter tube connection
520 ring
600 bendable body, deflecting portion
610 deflecting connection
620 deflecting cap
700 wire guiding ring

The invention claimed is:

1. A deflection movement transmission device having a proximal and a distal end and comprising
    a control element arranged at the proximal end of the deflection movement transmission device for effecting a deflection movement and comprising a pivot portion having an outer circumference,
    a base body, the control element being arranged such that the control element is pivotable relative to the base body
    an elongate transmission guiding body, and
    a bendable and deflectable body having a distal end and being arranged at the distal end of the deflection movement transmission device,
    wherein the control element comprises an inner channel through which the bendable body is guidable,
    the deflection movement transmission device further comprising
    at least one movement transmission wire body having a distal end and proximal end that is attached to the outer circumference of the pivot portion of the control element,
    the movement transmission wire body being guided through the elongate transmission guiding body along the longitudinal direction thereof,
    the distal end of the movement transmission wire body being attached to the distal end of the bendable body,
    a wire body guiding ring for guiding the movement transmission wire body and being inserted in the base body, the wire body guiding ring being movable relative to the base body for tensioning the movement transmission wire body by moving the wire body guiding ring along the base body.

2. The deflection movement transmission device according to claim 1,
    wherein the elongate transmission guiding body is arranged on a side of the base body, and
    the base body also comprises an inner channel through which the bendable body is guidable.

3. The deflection movement transmission device according to claim 2,
    wherein the inner channel is arranged concentrically in the control element, and/or
    the inner channel is arranged concentrically in the base body.

4. The deflection movement transmission device according claim 2, wherein
   at least a portion of the elongate transmission guiding body is guidable through the inner channel of the control element and/or the inner channel of the base body.

5. The deflection movement transmission device according to claim 2, wherein
   the control element pivot portion is supported on a head portion of the base body and is pivotable relative to the head portion of the base body for effecting a deflection movement,
   the pivot portion of the control element has an outlet communicating with the inner channel of the control element,
   the inner channel of the base body has an inlet opening in the head portion of the base body.

6. The deflection movement transmission device according to claim 5,
   wherein the control element is configured as an actuating lever having, at the pivot portion, a foot surface facing the base body,
   the head portion of the base element having a front face facing the control element,
   wherein at least the foot surface of the pivot portion of the control element and/or the front face of the head portion of the base element is curved such that the foot surface can be rolled on the front face,
   wherein the pivot portion of the control element has an attachment point of the movement transmission wire body on its outer side, and, with its foot surface, is pivotably seated on the front face of the head portion of the base element,
   wherein the foot surface of the pivot portion comprises the outlet opening of the inner channel of the control element, and the front face of the head portion comprises the inlet opening of the inner channel of the base body.

7. The deflection movement transmission device according to claim 5,
   wherein the control element is configured as an actuating lever which, at the pivot portion, turns into a hollow ball portion,
   wherein the head portion of the base element is formed spherically,
   wherein the hollow ball portion has an attachment point of the movement transmission wire body on its outer side and, on its inner ball surface, is slidably seated on the spherical head portion,
   wherein the hollow ball portion comprises the outlet opening of the inner channel of the control element and the spherical head portion comprises the inlet opening of the inner channel of the base body.

8. The deflection movement transmission device according to claim 1, wherein the control element is lockable so as to lock a deflected position of the control element.

9. The deflection movement transmission device according to claim 1, wherein one or more movement transmission wire bodies are provided, the first ends of which are equally spaced apart from each other and are attached to the control element, and the opposite second ends of which are fixed to the distal end portion of the body to be deflected in a corresponding manner equally spaced apart from each other.

10. An endoscope comprising a deflection movement transmission device, said deflection movement transmission device comprising
   a control element arranged at a proximal end of the deflection movement transmission device for effecting a deflection movement,
   a base body a which the control element for effecting a deflection movement is arranged such that a pivoting movement of the control element relative to the base body can be carried out,
   an elongate transmission guiding body, and
   a bendable body to be deflected that is arranged at a distal end of the deflection movement transmission device,
   wherein the control element comprises an inner channel through which the bendable body to be deflected is guidable,
   the deflection movement transmission device comprises at least one movement transmission wire body whose proximal end is attached to the outer circumference of a pivot portion of the control element,
   the movement transmission wire body is guided through the elongate transmission guiding body along the longitudinal direction thereof,
   the distal end of the movement transmission wire body is attached to the distal end of the bendable body to be deflected,
   a wire body guiding ring for guiding the movement transmission wire body is inserted in the base body, the wire body guiding ring being moveable relative to the base body for tensioning the movement transmission wire body by moving the wire body guiding ring along the base body;
   wherein the elongate transmission guiding body is a catheter tube, the bendable body to be deflected is a bending portion of the catheter tube, and the bending portion and a distal portion of the catheter tube can be guided through the inner channel of the control element.

* * * * *

UNITED STATES PATENT AND TRADEMARK OFFICE
CERTIFICATE OF CORRECTION

PATENT NO. : 10,076,233 B2
APPLICATION NO. : 15/033064
DATED : September 18, 2018
INVENTOR(S) : Thomas Viebach et al.

Page 1 of 1

It is certified that error appears in the above-identified patent and that said Letters Patent is hereby corrected as shown below:

On the Title Page

Item (54), change "*DEVICE FOR TRANSMITTING A DEFLECTION MOVEMENT, ENDOSCOPE BENDING CONTROL UNIT, AND ENDOSCOPE*" to --*DEFLECTION MOVEMENT TRANSMISSION DEVICE, ENDOSCOPE BENDING CONTROLLER AND ENDOSCOPE*--.

Item (72), change "*Freidrich Pauker*" to --*Friedrich Pauker*--.

In the Specification

In Column 3 at Line 38 (Approx.), change "*4,*" to --*4*--.

In the Claims

In Column 15 at Line 2, In Claim 4, after "according" insert --*to*--.

In Column 16 at Line 19 (Approx.), In Claim 10, change "*a*" to --*at*--.

Signed and Sealed this
Second Day of July, 2019

Andrei Iancu
*Director of the United States Patent and Trademark Office*